United States Patent
Mirigian

(10) Patent No.: US 6,682,493 B2
(45) Date of Patent: Jan. 27, 2004

(54) HIGH TORQUE GUIDEWIRE

(75) Inventor: Gregory E. Mirigian, Dublin, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/008,446

(22) Filed: Dec. 3, 2001

(65) Prior Publication Data

US 2003/0105415 A1 Jun. 5, 2003

(51) Int. Cl.⁷ .......................... A61B 5/00; A61M 25/00
(52) U.S. Cl. ................................................ 600/585
(58) Field of Search ........................... 600/585, 434; 15/104.33; 464/51; 604/164.3, 528; 74/502.5

(56) References Cited

U.S. PATENT DOCUMENTS

| | | |
|---|---|---|
| 3,674,014 A | 7/1972 | Tillander |
| 4,798,598 A | 1/1989 | Bonello et al. |
| 4,955,384 A * | 9/1990 | Taylor et al. ............... 600/434 |
| 4,985,022 A | 1/1991 | Fearnot et al. |
| 4,998,923 A | 3/1991 | Samson et al. |
| 5,003,989 A | 4/1991 | Taylor et al. |
| 5,095,915 A | 3/1992 | Engelson |
| 5,315,996 A | 5/1994 | Lundquist |
| 5,406,960 A | 4/1995 | Corso, Jr. |
| 5,437,288 A | 8/1995 | Schwartz et al. |
| 5,570,701 A | 11/1996 | Ellis et al. |
| 5,599,492 A | 2/1997 | Engelson |
| 5,746,701 A | 5/1998 | Noone |
| 5,749,837 A | 5/1998 | Palermo et al. |
| 5,769,796 A | 6/1998 | Palermo et al. |
| 5,772,609 A | 6/1998 | Nguyen et al. |
| 5,776,080 A | 7/1998 | Thome et al. |
| 5,833,632 A | 11/1998 | Jacobsen et al. |
| 5,902,254 A | 5/1999 | Magram |
| 5,931,830 A | 8/1999 | Jacobsen et al. |
| 5,951,494 A | 9/1999 | Wang et al. |
| 6,001,068 A | 12/1999 | Uchino et al. |
| 6,017,319 A | 1/2000 | Jacobsen et al. |
| 6,139,510 A | 10/2000 | Palermo |
| 6,273,876 B1 | 8/2001 | Klima et al. |

FOREIGN PATENT DOCUMENTS

EP     0 778 040     6/1997

* cited by examiner

Primary Examiner—Max F. Hindenburg
Assistant Examiner—Brian Szmal
(74) Attorney, Agent, or Firm—Crompton, Seager & Tufte, LLC

(57) ABSTRACT

Alternative designs, materials and manufacturing methods for medical devices such as guidewires. Some embodiments are directed to a guidewire, including a core wire having a proximal portion and a distal portion, and an elongated distal assembly defining an inner lumen, the elongated distal assembly connected to the core wire adjacent the distal portion of the core wire, wherein the elongated distal assembly includes a plurality of separate and discrete interlocking segments. Some other embodiments are directed to a guidewire including a tubular segment connected to the distal portion of the corewire, wherein the tubular segment includes a plurality of notches therein to increase the lateral flexibility of the segment while maintaining rotational torqueability.

23 Claims, 4 Drawing Sheets

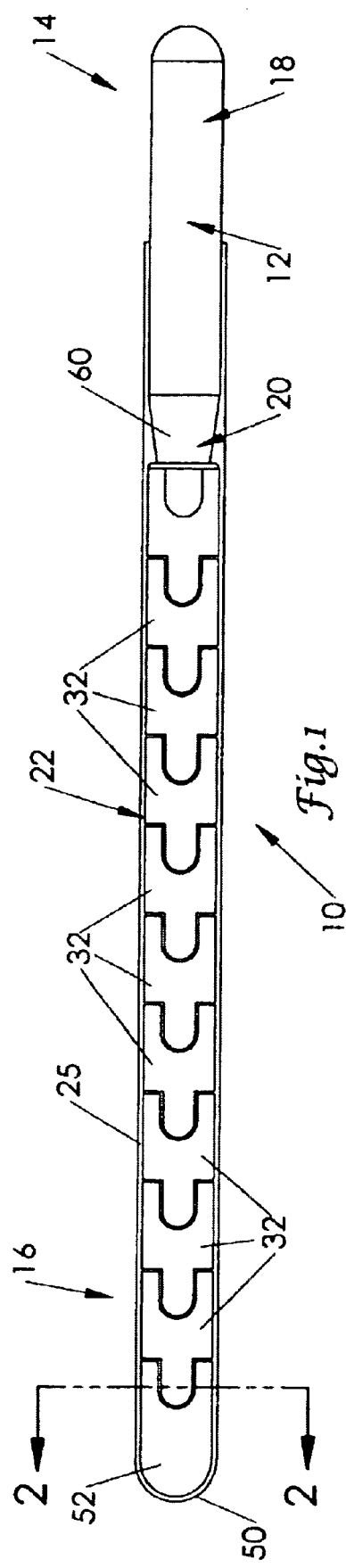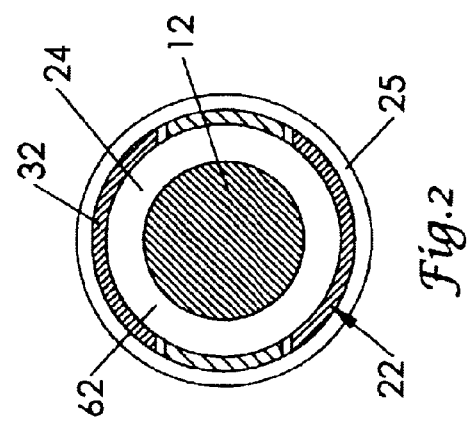

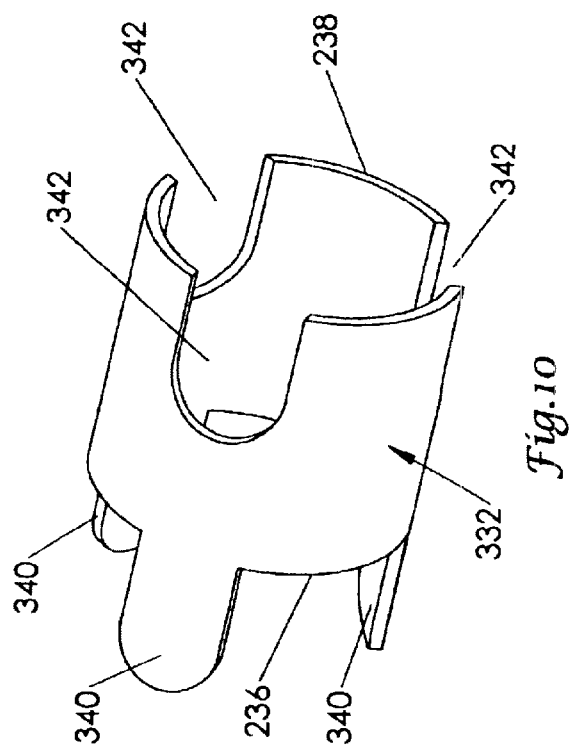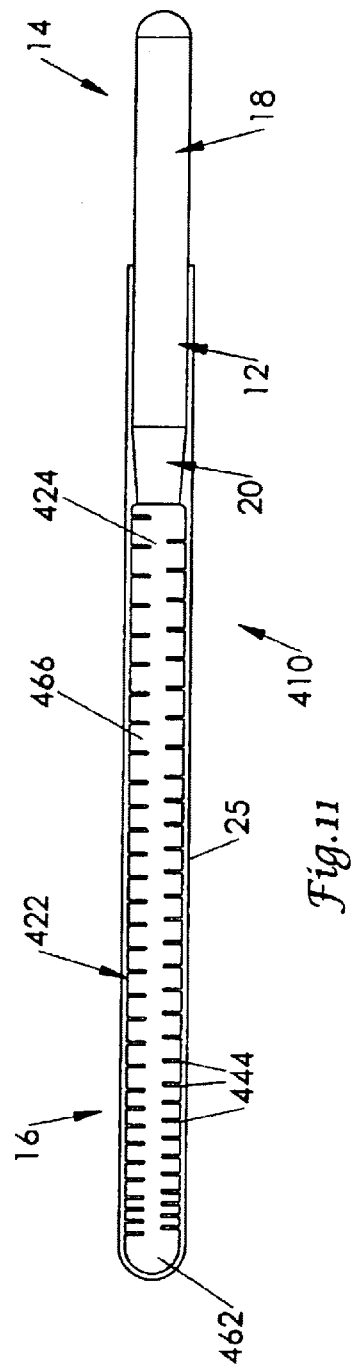

HIGH TORQUE GUIDEWIRE

FIELD OF THE INVENTION

The invention generally pertains to medical devices, and more particularly to medical guidewires such as intravascular guidewires.

BACKGROUND

Guidewires are commonly used in conjunction with intravascular devices, for example intravascular catheters or other such devices, to facilitate navigation through the vasculature of a patient. The vasculature of a patient may be very tortuous. It is often desired that certain portions of a guidewire have lateral flexibility characteristics as well as pushability and torqueability (tortional or rotational stiffness) characteristics.

SUMMARY

The invention provides several alternative designs, materials and manufacturing methods for medical devices such as guidewires. Some example embodiments include a guidewire including an elongated assembly or member adapted and configured to provide for lateral flexibility characteristics as well as torqueability characteristics.

BRIEF DESCRIPTION OF THE DRAWINGS

FIG. 1 is a partially fragmented side view of a guidewire in accordance with one example embodiment, with a portion of an outer layer on the distal section of the guidewire cut away to expose an elongated assembly including a plurality of interlocking segments, the assembly being connected to a core wire adjacent the distal portion thereof.

FIG. 2 is a cross sectional view of the guidewire of FIG. 1, taken along lines 2—2 of FIG. 1;

FIG. 10 is a perspective view of one interlocking member of yet another embodiment; and FIG. 11 is a partially fragmented side view of a guidewire in accordance with an alternative design, with a portion of an outer layer on the distal end of the guidewire cut away to expose a tubular member connected to the core wire adjacent the distal portion, and wherein the tubular member has a plurality of notches cut therein.

DETAILED DESCRIPTION OF SOME EMBODIMENTS

Figure 3:
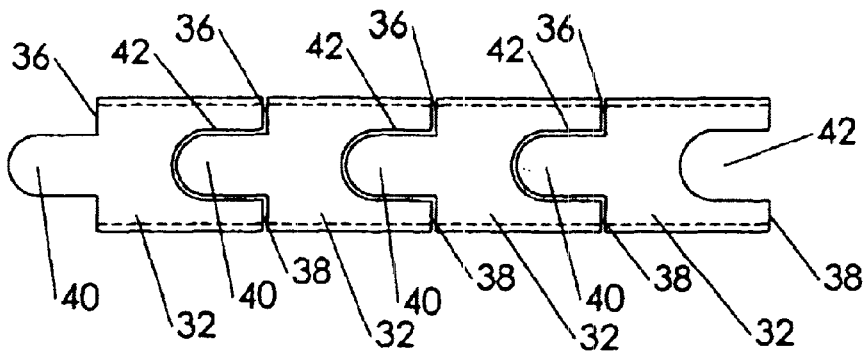
FIG. 3 is a side view of some of the interlocking segments of the guidewire of FIG. 1.

The following description should be read with reference to the drawings wherein like reference numerals indicate like elements throughout the several views. The detailed description and drawings illustrate examples of various embodiments, and are not intended to be limiting to the invention as claimed.

FIG. 1 shows a partially fragmented cross sectional side view of a portion of a guidewire 10 in accordance with one example embodiment. The guidewire 10 includes a proximal section 14 and a distal section 16. The guidewire 10 also includes a core wire 12 having a proximal portion 18 and a distal portion 20. An elongated hollow structure or assembly 22 made up of a plurality of individual interlocking segments 32 is disposed adjacent the distal portion 20 of the core wire 12, as will be discussed in more detail below. An outer sheath 25 is disposed about at least a portion of the assembly 22. In FIG. 1, a portion of the outer sheath 25 has been cut away to show the assembly 22. In the embodiment shown, at least a portion of the core wire 12 is disposed within an inner lumen 24 defined by the elongated assembly 22 as shown in FIG. 2. FIG. 2 shows a cross sectional view of the guidewire of FIG. 1, taken along line 2—2 of FIG. 1, and illustrating a portion of the core wire 12 within the inner lumen 24 of the elongated assembly 22. The guidewire 10 typically has a total length in the range of about 50 and about 300 centimeters.

The core wire 12 can include any suitable structure for use as a core wire, as will be understood by those of skill in the art and others. The core wire 12 can have a solid cross-section as shown, but in some embodiments, can have a hollow cross-section. In yet other embodiments, the core wire 12 can include a combination of areas having solid cross-sections and hollow cross sections.

The core wire 12 can be continuously tapered, can have a tapered section or a number or series of tapered sections of differing diameters, or can have a constant diameter. In some embodiments, the core wire 12 is tapered or otherwise formed to have a geometry that decreases in cross sectional area toward the distal end thereof. If tapered, the core wire 12 can include a uniform or a non-uniform transition of the sections, depending on the transition characteristics desired. For example, the core wire 12 may be linearly tapered, tapered in a curvilinear fashion, or tapered in a step-wise fashion. The angle of any such tapers can vary, depending upon the desired flexibility characteristics. The length of the taper may be selected to obtain a more (longer length) or less (shorter length) gradual transition in stiffness.

In some embodiments, the structure used to construct the core wire 12 is designed such that the proximal portion 18 can be relatively stiff for pushability and torqueability, and the distal portion 20 can be relatively flexible by comparison for better lateral trackability and steerability. For example, in some embodiments, the proximal portion 18 has a constant or generally uniform diameter along its length to enhance stiffness. However, embodiments including a proximal portion having a tapered portion or a series of tapered portions are also contemplated. The diameter of the proximal portion 18 of the core wire 12 is sized appropriately for the desired stiffness characteristics dependent upon the material used. For example, in some embodiments, the proximal portion 18 has a diameter in the range of about 0.010 to about 0.025 inches, and in some embodiments, in the range of about 0.010 to about 0.018 inches.

The distal portion 20 can likewise be constant diameter, can be continuously tapered, or can have a tapered section or a number or a series of tapered sections of differing diameters. In embodiments where the structure of the core wire 12 is designed such that the distal portion 20 is relatively flexible by comparison to the proximal portion 18, the distal portion 20 typically does include at least one tapered or reduced diameter portion for better flexibility characteristics. In the embodiment shown, the distal portion 20 includes at least one tapered portion 60.

The lengths of the proximal and distal portions 18/20 are typically dictated by the length and flexibility characteristics desired in the final guidewire. In some embodiments, the proximal portion 18 typically has a length in the range of about 50 to about 300 centimeters, and the distal portion 20 typically has a length in the range of about 3 to about 50 centimeters.

The core wire 12 can be made of any material suitable for core wire construction, as will be understood by those of skill in the art and others. Some examples of suitable materials include metals, metal alloys, polymers, or the like, or combinations or mixtures thereof. Some examples of suitable metals and metal alloys include stainless steel, such as 304v stainless steel, nickel-titanium alloy, such as nitinol, nickel-chromium alloy, nickel-chromium-iron alloy, cobalt alloy, or the like, or other suitable material. The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL).

The entire core wire 12 can be made of the same material, or in some embodiments, the core wire 12 can include portions or sections made of different materials. In some embodiments, the material used to construct the core wire 12 is chosen to impart varying flexibility and stiffness characteristics to different portions of the core wire 12. For example, the proximal core wire portion 18 and the distal core wire portion 20 may be formed of different materials (i.e., materials having different moduli of elasticity) resulting in a difference in flexibility. For example, the material used to construct the proximal portion 18 can be relatively stiff for pushability and torqueability, and the material used to construct the distal portion 20 can be relatively flexible by comparison for better lateral trackability and steerability. In one embodiment, the proximal portion 18 can be formed of relatively stiff material, for example, straightened 304v stainless steel wire, and the distal portion 20 can be formed of a relatively flexible material, for example a straightened super elastic or linear elastic alloy (e.g., nickel-titanium) wire.

In embodiments where different portions of the core wire 12 are made of different material, the different portions are connected using any suitable connecting techniques. For example, the different portions of the core wire can be connected using welding, soldering, brazing, adhesive, or the like, or combinations thereof. Additionally, some embodiments can include one or more mechanical connectors or connector assemblies to connect the different portions of the core wire that are made of different materials. The connector may comprise any structure generally suitable for connecting portions of a guidewire. One example of a suitable structure includes a structure such as a hypotube or a coiled wire which has an inside diameter sized appropriately to receive and connect to the ends of the proximal portion 18 and the distal portion 20.

Referring still to FIG. 1, the guidewire 10 also includes the elongated assembly 22 connected to the core wire 12 adjacent the distal portion 20 of the core wire 12. In FIG. 1, a portion of an outer layer or sheath 25 has been cut away so that the elongated structure or assembly 22 can be viewed. The assembly 22 is a generally hollow structure defining an inner lumen 24 (FIG. 2). In some respects, the assembly 22 can be characterized as a tubular assembly. However, the term "tubular" is meant only to indicate that the assembly 22 is a generally elongated assembly that is generally hollow or defines an inner lumen in cross section. Those of skill in the art and others will recognize that the cross sectional shape of a structure 22 can vary, and is not necessarily circular or oval, and that other cross sectional shapes can be used. For example, the cross sectional shape of the assembly 22 can be multisided in geometry. In the embodiment shown, the assembly 22 has a generally circular cross section.

The assembly 22 includes a plurality of interlocking members or segments 32. In at least some embodiments, each of the segments 32 is typically a separate and discrete structure, independent from any adjacent segment or segments. Each of the plurality of interlocking segments 32 are adapted and configured to interlock with one or more segments that are adjacent thereto to inhibit rotation of adjacent segments relative to one another. This allows for transmission of torque along the elongated tubular assembly 22 in both rotational directions, while also allowing lateral flexure of the tubular assembly.

The number of segments 32 used to construct the assembly 22 is dependent upon the desired length and flexibility characteristics of the assembly 22. Some embodiments include three or more, ten or more, fifty or more, one hundred or more, or one hundred and fifty or more individual interlocking segments 32. Additionally, the length of each segment can also be varied dependent upon the desired torqueability and flexibility characteristics of the assembly 22. In some embodiments, the segments can range in length from about 0.5 millimeters to about 10 millimeters. All of the segments 32 within an assembly 22 can be of generally uniform length, or can vary in length to achieve variable stiffness characteristics along the length of the assembly 22. The total length of the assembly 22 can be in the range of about 3 to about 50 millileters and in some embodiments in the range of about 20 to about 50 millimeters.

The segments 32 can be made of any material suitable for construction of such structures, as will be understood by those of skill in the art and others. Some examples of suitable materials include metals, metal alloys, polymers, ceramics, or the like, or combinations or mixtures thereof. Some examples of suitable metals and metal alloys include stainless steel, such as 304v stainless steel, nickel-titanium alloy, such as nitinol, nickel-chromium alloy, nickel-chromium-iron alloy, cobalt alloy, or the like, or other suitable material.

Typically, each of the segments 32 is a hollow or generally tubular segment that includes interlocking features to prevent rotation of the segments relative to one another. Such interlocking features can include any structure generally known to provide such an interlocking function. For example, each of the segments 32 can include side surfaces including interlocking means, for example, crenations, teeth, serrations, bends, grooves, protrusions, notches, tongue and groove arrangements, or other arrangements, and the like, that are adapted and configured to mate with each other such that side surfaces of adjacent segments interlock in a mechanical or frictional manner to inhibit rotation of adjacent segments in relation to one another.

Figure 4:
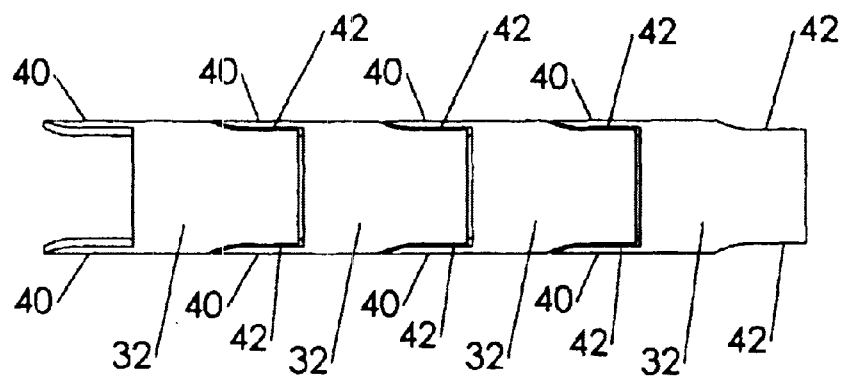
FIG. 4 is a different side view of the interlocking segments of FIG. 3, wherein the interlocking segments of FIG. 3 have been rotated ninety degrees to view a different side of the interlocking segments.
Figure 5:
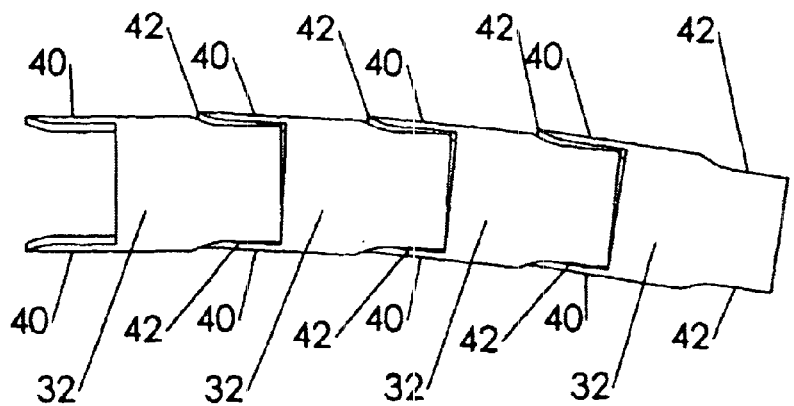
FIG. 5 is a side view of the interlocking segments of FIG. 4, showing the interlocking segments in a laterally biased position in relation to one another.

For example, the specific structure of the embodiment shown in FIGS. 1–5, and with reference specifically to FIGS. 3–5, each of the segments 32 includes side surfaces 36 and 38. The side surfaces 36 include a pair of protrusions 40, and the side surfaces 38 define a pair of notches 42 therein. The protrusions 40 are adapted and configured to mate with the notches 42 to provide a mechanical interlock between adjacent segments 32, and thereby inhibit rotation of adjacent segments 32 in relation to one another. In this embodiment, each of the notches 42 is generally laterally in line with one of the protrusions 40 on each of the segments 32. Therefore, as seen in FIG. 3, the notches 42 and the protrusions 40 of the multiple segments 32 are generally in line with each other along the length of the assembly 22. FIG. 4 is an alternative side view of the interlocking segments 32 of FIG. 3, showing the side when the segments 32 are rotated ninety degreed from the side shown in FIG. 3. As seen in FIG. 4, the pair of notches 42 and the pair of protrusions 40 on each segment are generally opposite each other about the outer surface of each segment 32. Therefore, as seen in FIG. 4, two rows of in line interlocking notches 42 and protrusions 40 are formed along the length of the assembly 22. FIG. 5 shows the interlocking segments 32 of FIG. 4, in a laterally bent or biased position. As can be seen in FIG. 5, the interlocking construction allows for lateral flexibility. However, due to the interlocking nature of the segments 32, the structure also provides for torqueability or tortional stiffness, to allow transmission of torque along the distal portion of the guidewire 12.

Referring again to FIG. 1, the assembly 22 is connected to the core wire 12 adjacent to the distal portion 20 of the core wire 12. In some embodiments, the core wire 12 does not extend into the lumen 24 of the assembly 22, and the assembly 22 is attached to a distal end of the core wire 12. In this embodiment, however, a portion of the core wire 12 is disposed within the lumen 24 defined by the assembly 22, and the core wire 12 is attached to at least one of the segments 32 to connect the assembly 22 to the core wire 12. In some embodiments, the core wire 12 is attached to the most proximal of the segments 32 that make up the assembly 22. In FIG. 1, the most proximal of the segment 32 of the assembly 22 is connected to the tapered portion 60 of the core wire 12. The attachment is made using any suitable attachment method. Examples of suitable attachment methods include welding, soldering, brazing, adhesive, shrink tubing, or the like, or combinations thereof.

The distal end of the core wire 12 can be free within the lumen 24 of the assembly 22, or can also be connected in some manner to the assembly 22. In embodiments where the distal end of the core wire 12 is connected to the assembly 22, it can be connected to the most distal segment 32 of the assembly 22. In FIG. 1, the most distal segment includes a distal surface 50 defined by an end cap 52. The distal end of the core wire 12 can be attached directly to an inner surface of the end cap 52 using suitable attachment techniques, for example welding, soldering, brazing, adhesive, or the like, or combinations thereof. In some embodiments, the distal end of the core wire 12 can be connected to the end cap 52 via a thin ribbon of material, for example a metallic ribbon. The ribbon would be attached to the end cap 52 and to the distal end of the core wire 12 using any suitable attachment technique, for example welding, soldering, brazing, adhesive, or the like, or combinations thereof. In some embodiments, the end cap 52 may be comprised from the attachment matter itself, for example, solder, an adhesive or the like.

As shown in FIG. 2, a portion of the core wire 12 is disposed within the lumen 24 defined by the elongated assembly 22, and a space or void 62 can be left between the core wire 12 and the inner surface of the assembly 22. In some embodiments, this void 62 is left open. In other embodiments, the void 62 can be partially or wholly filled with a filler material, such as a polymer or other suitable materials. In some embodiments, the filler material can include, or be doped with, radiopaque material to make the distal portion of the guidewire more visible when using certain imaging techniques, for example, fluoroscopy techniques. Any suitable radiopaque material known in the art can be used. Some examples include tungsten, barium powder, and the like, and mixtures thereof. In some embodiments, it is also contemplated that a separate radiopaque member or a series of radiopaque members, such as radiopaque coils, bands, tubes, or other such structures could be attached to the core wire within the void 62 to enhance the imaging of the guidewire 10.

The guidewire 10 also includes an outer sheath 25. The outer sheath 25 is disposed about at least a portion of the elongated assembly 22. In some embodiments, the outer sheath 25 is also disposed about at least a portion of the core wire 12. Referring to FIG. 1, the outer sheath 25 is disposed about the entire length of the elongated assembly 22, and extends onto a portion of the core wire 12. The outer sheath 25 is disposed over the elongated assembly 22, and can encapsulate and maintain the interlocking segments 32 in position within the assembly 22, yet allow the assembly 22 to flex and bend laterally. The sheath 25 can include one or more layers of material.

Suitable material for use as the outer sheath 25 include any material that would give the desired adhesion, flexibility or other desired characteristics. Some suitable materials include polymers, and like material. Examples of suitable polymer material for use as the outer sheath 25 can include any of a broad variety of polymers generally known for use on guidewires, and which have the desired characteristics. For example, the outer sheath 25 can include polymer materials and structures generally known for use in guidewire core coatings or tie layers between guidewire core coatings and guidewire cores. Some examples of such coatings and tie layers and materials and methods used to create such tie layers and coating can be found in U.S. Pat. Nos. 6,139,510 and 5,772,609, which are incorporated herein by reference.

Figure 6:
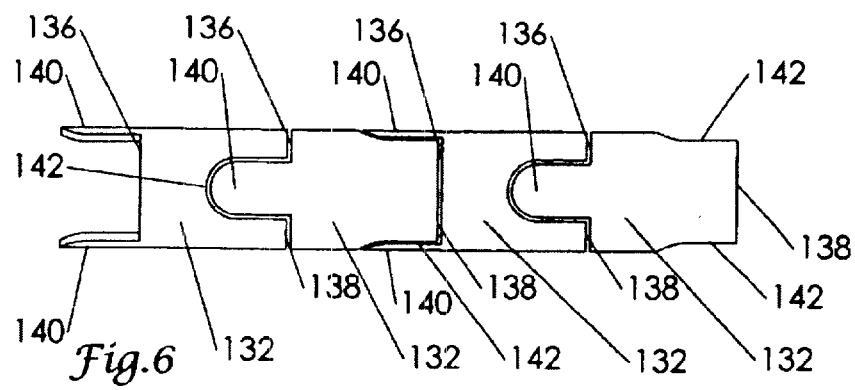
FIG. 6 is a side view of some of the interlocking segments of another example embodiment, wherein the interlocking features on each of the segments are disposed in alternating positions such that the interlocking features are not consecutively in line.

FIG. 6 shows an alternative embodiment of interlocking segments 132 that could be incorporated into an elongated assembly 22 on the distal end of a guidewire 10 in a similar manner as discussed above in relation to the embodiment shown in FIGS. 1–5. In this embodiment, the interlocking segments include side surfaces 136 and 138 including a pair of protrusions 140 and a pair of notches 142, respectively, similar to those shown in FIGS. 3–5. The protrusions 140 are adapted and configured to mate with the notches 142 to provide a mechanical interlock between adjacent segments 132, and thereby inhibit rotation of adjacent segments 132 in relation to one another. However, in this embodiment, each of the notches 142 are not laterally in line with the protrusions 140 on each of the segments 132. The notches 142 on each segment 132 are offset from the protrusions 140.

Therefore, as seen in FIG. 6, the interlocking notches 142 and protrusions 140 of the multiple segments 32 generally alternate in radial position from one segment to the next, and are not consecutively in line with each other along the length of the assembly 22.

Figure 7:
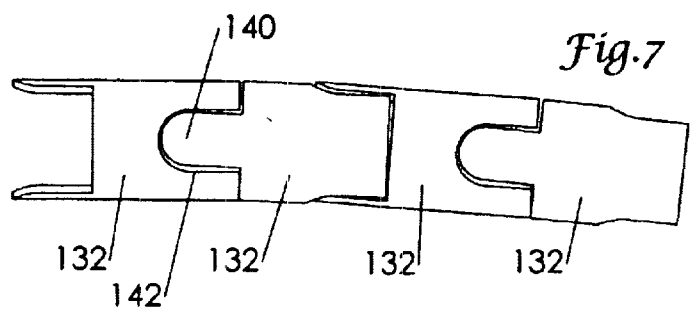
FIG. 7 is a side view of the interlocking segments of FIG. 6, showing the interlocking segments in a laterally biased position in relation to one another.

FIG. 7 shows the interlocking segments 132 of FIG. 6, in a bent or biased position. As can be seen in FIG. 7, the interlocking construction allows for lateral flexibility. However, due to the interlocking nature of the segments, the structure also provides for torqueability or tortional stiffness, to allow transmission of torque along the distal portion of the guidewire 12.

Figure 8:
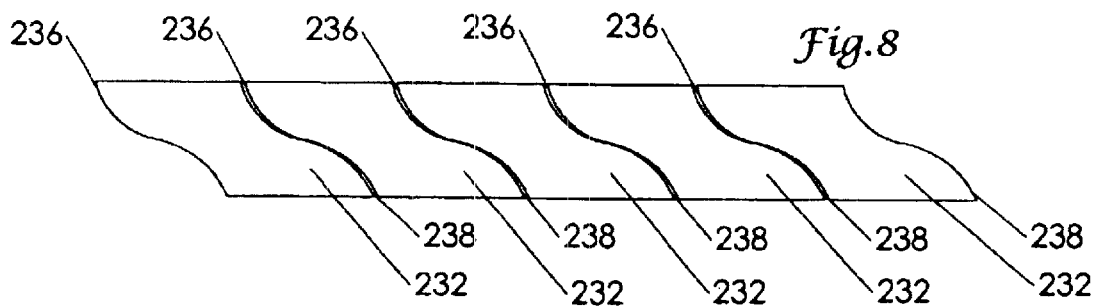
FIG. 8 is a side view of some of the interlocking segments of another example embodiment, showing a different shape to the interlocking segments.

FIG. 8 shows another alternative embodiment of interlocking segments 232 that could be incorporated into an elongated assembly 22 on the distal end of a guidewire 10 in a similar manner as discussed above in relation to the embodiment shown in FIGS. 1–5. In this embodiment, the interlocking segments 232 include side surfaces 236 and 238 that are configured to have a non-linear or curved shape. The curved shape of the side surfaces 236 of one segment is adapted and configured to be complementary to, and interlocking with, the curved shape of the side surface 238 of the next adjacent segment. As such, the curved side surfaces 236 and 238 provide an interlocking feature to prevent rotation of adjacent segments relative to one another. In the embodiment shown, the curved surfaces are somewhat in the shape of an "S" when viewed from one side, however, other configurations of the curved surfaces are contemplated, and will be readily apparent to those of skill in the art.

Figure 9:
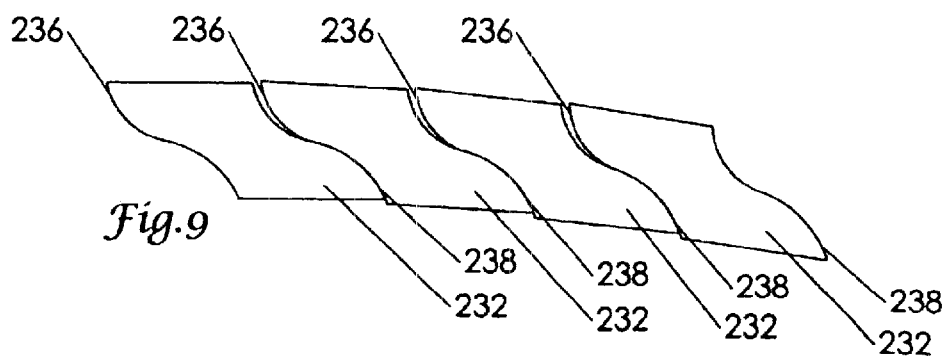
FIG. 9 is a side view of the interlocking segments of FIG. 8, showing the interlocking segments in a laterally biased position in relation to one another.

FIG. 9 shows the interlocking segments 232 of FIG. 8, in a bent or biased position. As can be seen in FIG. 9, the interlocking construction allows for lateral flexibility. However, due to the interlocking nature of the segments 232, the structure also provides for torqueability or tortional stiffness, to allow transmission of torque along the distal portion of the guidewire 12.

FIG. 10 is a perspective view of one interlocking member 332 of yet another embodiment. A plurality of such interlocking segments 232 could be incorporated into an elongated assembly 22 on the distal end of a guidewire 10 in a similar manner as discussed above in relation to the embodiment shown in FIGS. 1–5. In this embodiment, the interlocking segment 332 includes side surfaces 336 and 338 having three protrusions 340 and three notches 342, respectively. The protrusions 340 and notches 342 are similar in structure to those notches and protrusions shown in the embodiment of FIGS. 1–5. The protrusions 340 are adapted and configured to mate with the notches on an adjacent similar interlocking member, and the notches 342 are likewise adapted and configured to mate with the protrusions on another adjacent similar locking member, to provide a mechanical interlock between adjacent segments, and thereby inhibit rotation of adjacent segments in relation to one another. This embodiment illustrates that more than a pair of such interlocking features can be included on a side of an interlocking segment. It should also be understood that in other embodiments, less than a pair of such interlocking features can be can be included on a side of an interlocking segment.

FIG. 11 shows a partially fragmented cross sectional side view of a portion of a guidewire 410 in accordance with another design. The guidewire 410 is similar to the embodiment shown in FIG. 1, and includes proximal section 14 and a distal section 16. The guidewire 410 also includes a core wire 12 having a proximal portion 18 and a distal portion 20. The core wire 12 can have the same configuration and can be made of the same materials as discussed above with regard to the embodiment shown in FIGS. 1–5.

This design, however, includes an elongated tubular member 422 having one or more, and in most embodiments, a plurality of axially spaced notches or grooves 444 formed therein. The tubular member 422 is connected to the core wire 12 adjacent the distal portion 20. The tubular member 422 defines an outer surface 466 and an inner lumen 424. In some embodiments, the tubular member can be a hypotube having a rounded distal end 462. The length of the tubular member 422 can be in the range of about 3 to about 50 millimeters, and in some embodiments, in the range of about 20 to about 50 millimeters.

The notches 444 act to enhance the lateral flexibility of the tubular member 422 while allowing the rotational torqueability of the tubular member 422 to be maintained. In at least some embodiments, at least some of the notches 444 extend through the outer surface 466 into the inner lumen 424. In some embodiments, the notches 444 are laid out in a predetermined pattern to enhance the lateral flexibility characteristics of certain portions of the tubular member 422. For example, the axial spacing of the notches 444 or the size of the notches 444 can be varied along the length of the tubular member 422 to vary the flexibility characteristics. In general, lateral flexibility is increased as the axial spacing is decreased, and the size of the notches is increased. Conversely, lateral flexibility is decreased as the axial spacing between notches is increased and the size of the notches are decreased. In the embodiment shown, the axial spacing between notched 444 is decreased near the distal portion of the tubular member 422 to increase the lateral flexibility at the distal end.

Axial spacing between grooves can range from about 0.2 mm to about 10 mm, and in some embodiments from about 0.2 mm to about 2 mm. The width of the grooves can range from about 0.1 mm to about 2 mm, and in some embodiments from about 0.2 mm to about 1 mm.

The tubular member 422 can be made of the same variety of materials as discussed above with regard to the materials used in the segments of the elongated assembly 22 in the embodiment of FIGS. 1–5. Additionally, the tubular member 422 can be attached to the core wire 12 using a similar configuration and using similar materials as discussed above with regard to the attachment of the elongated assembly in the embodiment of FIGS. 1–5 to the core wire 12. Furthermore, similar to the embodiment of FIGS. 1–5, an outer sheath 25 is disposed about at least a portion of the tubular member 422. In FIG. 11, a portion of the outer sheath 25 has been cut away to show the elongated tubular member 422. The outer sheath 25 can have essentially the same configuration and can be made of the same materials as discussed above with regard to the embodiment of FIGS. 1–5.

It should be understood that this disclosure is, in many respects, only illustrative. Changes may be made in details, particularly in matters of shape, size, and arrangement of steps without exceeding the scope of the invention. For example, it should be understood by those of skill in the art and others that many interlocking structures are contemplated for use in the elongated assembly. Embodiments similar to those shown above, but having more or fewer interlocking features are possible. Furthermore, although discussed with specific reference to guidewires, the invention may be applicable to other medical devices having a need for a distal portion with both characteristics of lateral flexibility and tortional stiffness. For example, the present invention may be applicable for use in intravascular catheters (e.g., rapid exchange balloon catheters, stent delivery catheters, etc.) or intravascular rotational devices (atherectomy catheters, IVUS catheters, etc.). The invention's scope is, of course, defined in the language in which the appended claims are expressed.

What is claimed is:

1. A guidewire, comprising:
   a core wire having a proximal portion and a distal portion; and
   an elongated distal assembly defining an inner lumen, the elongated distal assembly connected to the core wire adjacent the distal portion of the core wire, wherein the elongated distal assembly includes a plurality of separate and discrete interlocking segments that are each configured to prevent rotation of segments relative to adjacent segments without limiting axial movement therebetween.

2. The guidewire of claim 1, wherein the elongated assembly is connected to the core wire such that at least a portion of the core wire extends into at least a portion of the lumen defined by the elongated assembly.

3. The guidewire of claim 1, wherein the interlocking segments are hollow tubular segments.

4. The guidewire of claim 1, wherein the interlocking segments include interlocking features that the prevent rotation of the segments relative to adjacent segments.

5. The guidewire of claim 1, wherein the interlocking segments include side surfaces which define interlocking members or grooves for interlocking with adjacent segments.

6. The guidewire of claim 1, wherein the interlocking segments are adapted and configured to allow for lateral flexure of the elongated distal assembly.

7. The guidewire of claim 1, wherein the elongated distal assembly comprises ten or more separate and discrete interlocking segments.

8. The guidewire of claim 1, wherein the elongated distal assembly comprises one hundred or more separate and discrete interlocking segments.

9. The guidewire of claim 1, wherein the guidewire further includes an outer sheath disposed about at least a portion of the elongated assembly.

10. The guidewire of claim 9, wherein the outer sheath also extends about at least a portion of the core wire.

11. The guidewire of claim 9, wherein the outer sheath comprises a polymer.

12. The guidewire of claim 9, wherein the outer sheath encapsulates and maintains the interlocking segments in position within the elongated assembly.

13. The guidewire of claim 1, wherein each of the plurality of separate and discrete interlocking segments has a length in the range of about 0.5 millimeters to about 10 millimeters.

14. The guidewire of claim 1, wherein the core wire comprises a wire having a solid cross section.

15. The guidewire of claim 1, wherein the distal portion of the core wire includes a tapered portion, and the elongated distal assembly is connected to the distal portion adjacent the tapered portion.

16. The guidewire of claim 1, wherein the separate and discrete interlocking segments interlock with one another and are adapted and configured to allow transmission of torque along the elongated assembly in both rotational directions, while also allowing lateral flexure.

17. The guidewire of claim 1, wherein the interlocking segments include parallel side surfaces that form interlocking members and also include parallel side surfaces that form grooves, where the interlocking member of one segment interacts with the groove of an adjacent segment.

18. A guidewire, comprising:
    a core wire having a proximal portion and a distal portion; and
    an elongated tubular assembly connected to the core wire adjacent to the distal portion of the core wire, wherein the elongated tubular assembly includes a plurality of separate and discrete interlocking tubular segments that are adapted and configured to interlock with one another to inhibit adjacent interlocking segments from rotating relative to one another to thereby allow transmission of torque along the elongated tubular assembly in both rotational directions without limiting axial movement between adjacent interlocking segments, while also allowing lateral flexure.

19. The guidewire of claim 18, wherein the guidewire further includes an outer sheath disposed about at least a portion of the elongated tubular assembly.

20. The guidewire of claim 18, wherein the interlocking segments include parallel side surfaces that form interlocking members and also include parallel side surfaces that form grooves, where the interlocking member of one segment interacts with the groove of an adjacent segment.

21. A guidewire, comprising:
    a core wire having a proximal portion and a distal portion; and
    an elongated assembly connected to the core wire adjacent the distal portion of the core wire, the elongated assembly including means for allowing transmission of torque along the elongated assembly in both rotational directions while not limiting axial movement within the elongated assembly, while also allowing lateral flexure.

22. A medical device, comprising:
    a core wire having a proximal portion and a distal portion, wherein the distal portion has a solid cross-section; and
    an elongated tubular distal assembly defining an inner lumen, the elongated distal assembly connected to the core wire adjacent the distal portion of the core wire, wherein the elongated tubular distal assembly includes a plurality of separate and discrete interlocking tubular segments that are each configured to prevent rotation of segments relative to adjacent segments without limiting relative axial movement.

23. The medical device of claim 22, wherein the interlocking segments include parallel side surfaces that form interlocking members and also include parallel side surfaces that form grooves, where the interlocking member of one segment interacts with the groove of an adjacent segment.

* * * * *

UNITED STATES PATENT AND TRADEMARK OFFICE
CERTIFICATE OF CORRECTION

PATENT NO.    : 6,682,493 B2
DATED         : January 27, 2004
INVENTOR(S)   : Mirigian It is certified that error appears in the above-identified patent and that said Letters Patent is hereby corrected as shown below:

<u>Column 9,</u>
Line 26, delete "the".

Signed and Sealed this

Thirteenth Day of April, 2004

JON W. DUDAS
*Acting Director of the United States Patent and Trademark Office*